United States Patent
Cheon et al.

(10) Patent No.: US 7,807,607 B2
(45) Date of Patent: Oct. 5, 2010

(54) COLOR-FORMING COMPOUNDS AND USE THEREOF IN IMAGING MEMBERS AND METHODS

(75) Inventors: Kap-Soo Cheon, Shrewsbury, MA (US); Michael P. Filosa, Medfield, MA (US); Fariza Hasan, Waltham, MA (US); Xavier Herault, Maynard, MA (US); John L. Marshall, Lexington, MA (US)

(73) Assignee: Zink Imaging, Inc., Bedford, MA (US)

( * ) Notice: Subject to any disclaimer, the term of this patent is extended or adjusted under 35 U.S.C. 154(b) by 93 days.

(21) Appl. No.: 12/343,234

(22) Filed: Dec. 23, 2008

(65) Prior Publication Data

US 2009/0137389 A1    May 28, 2009

Related U.S. Application Data

(63) Continuation-in-part of application No. 11/433,810, filed on May 12, 2006, and a continuation-in-part of application No. 11/433,808, filed on May 12, 2006.

(51) Int. Cl.
  *B41M 5/327* (2006.01)
(52) U.S. Cl. ............... 503/221; 106/31.22; 549/302
(58) Field of Classification Search .......... None
  See application file for complete search history.

(56) References Cited

U.S. PATENT DOCUMENTS

| | | |
|---|---|---|
| 2,417,897 A | 3/1947 | Adams |
| 3,488,705 A | 1/1970 | Fox et al. |
| 3,539,375 A | 11/1970 | Baum |
| 3,745,009 A | 7/1973 | Jenkins et al. |
| 3,832,212 A | 8/1974 | Jenkins et al. |
| 3,929,831 A | 12/1975 | Garner et al. |
| RE29,168 E | 4/1977 | Heseltine et al. |
| 4,097,288 A | 6/1978 | Lawton |
| 4,226,912 A | 10/1980 | Iwasaki et al. |
| 4,232,552 A | 11/1980 | Hof et al. |
| 4,243,052 A | 1/1981 | Bailey |
| 4,264,701 A | 4/1981 | Locatell, Jr. et al. |

(Continued)

FOREIGN PATENT DOCUMENTS

DE    96 668 C    7/1898

(Continued)

OTHER PUBLICATIONS

Masahiko et al., "New Thermo-Response Dyes: Coloration by the Claisen Rearrangement and Intromolecular Acid-Base Reaction", Angew. Chem. Int. Ed. Engl., 1992, vol. 31, pp. 204-205.

(Continued)

*Primary Examiner*—Bruce H Hess
(74) *Attorney, Agent, or Firm*—Foley & Lardner LLP; James F. Ewing; Michel Morency

(57) ABSTRACT

There are described novel rhodamine color-forming compounds. The rhodamine color-forming compounds exhibit a first color when in a crystalline form and a second color, different from the first color, when in an amorphous form. Thermal imaging members containing these color-formers are also described.

13 Claims, 1 Drawing Sheet

U.S. PATENT DOCUMENTS

| | | | |
|---|---|---|---|
| 4,380,629 | A | 4/1983 | Yamashita et al. |
| 4,390,616 | A | 6/1983 | Sato et al. |
| 4,401,717 | A | 8/1983 | Ikeda et al. |
| 4,405,788 | A | 9/1983 | Locatell, Jr. et al. |
| 4,415,633 | A | 11/1983 | Nakamura et al. |
| 4,436,920 | A | 3/1984 | Sato et al. |
| 4,544,936 | A | 10/1985 | Yokoi |
| 4,554,936 | A | 11/1985 | Tingley |
| 4,602,263 | A | 7/1986 | Borror et al. |
| 4,636,819 | A | 1/1987 | Nagamoto et al. |
| 4,641,147 | A | 2/1987 | Sakura et al. |
| 4,720,449 | A | 1/1988 | Borror et al. |
| 4,728,633 | A | 3/1988 | Satomura et al. |
| 4,803,148 | A | 2/1989 | Harada et al. |
| 4,826,976 | A | 5/1989 | Borror et al. |
| 5,177,262 | A | 1/1993 | Taylor et al. |
| 5,256,619 | A | 10/1993 | Yoshida et al. |
| 5,278,031 | A | 1/1994 | Boggs et al. |
| 5,338,644 | A | 8/1994 | Taylor et al. |
| 5,350,870 | A | 9/1994 | Boggs et al. |
| 5,395,948 | A | 3/1995 | Zink |
| 5,401,619 | A | 3/1995 | Boggs et al. |
| 5,427,996 | A | 6/1995 | Motoda et al. |
| 5,534,393 | A | 7/1996 | Boggs et al. |
| 5,559,075 | A | 9/1996 | Leenders et al. |
| 5,663,115 | A | 9/1997 | Naito et al. |
| 5,667,943 | A | 9/1997 | Boggs et al. |
| 5,869,420 | A | 2/1999 | Naito |
| 6,010,808 | A | 1/2000 | Naito et al. |
| 6,054,246 | A | 4/2000 | Bhatt et al. |
| 6,162,931 | A | 12/2000 | Gee et al. |
| 6,165,706 | A | 12/2000 | Fujiwara et al. |
| 6,229,055 | B1 | 5/2001 | Klaubert et al. |
| 6,420,131 | B1 | 7/2002 | Miller et al. |
| 6,537,410 | B2 | 3/2003 | Amost et al. |
| 6,801,233 | B2 | 10/2004 | Bhatt et al. |
| 6,951,952 | B2 | 10/2005 | Cheon et al. |
| 7,008,759 | B2 | 3/2006 | Cheon et al. |
| 7,098,168 | B2 | 8/2006 | Iwasaki et al. |
| 7,176,161 | B2 | 2/2007 | Chu et al. |
| 7,220,868 | B2 | 5/2007 | Cheon et al. |
| 7,279,264 | B2 | 10/2007 | Cheon et al. |
| 7,282,317 | B2 | 10/2007 | Allen et al. |
| 7,408,563 | B2 | 8/2008 | Busch et al. |
| 7,504,360 | B2 | 3/2009 | Chu et al. |
| 2004/0171817 | A1 | 9/2004 | Allen et al. |
| 2004/0176248 | A1 | 9/2004 | Chu et al. |
| 2004/0176617 | A1 | 9/2004 | Cheon et al. |
| 2004/0191668 | A1 | 9/2004 | Cheon et al. |
| 2004/0204317 | A1 | 10/2004 | Cheon et al. |
| 2006/0232642 | A1 | 10/2006 | Busch et al. |
| 2006/0293185 | A1 | 12/2006 | Filosa et al. |
| 2006/0293523 | A1 | 12/2006 | Filosa et al. |
| 2007/0123421 | A1 | 5/2007 | Chu et al. |
| 2007/0224552 | A1 | 9/2007 | Cheon et al. |
| 2008/0058524 | A1 | 3/2008 | Cheon et al. |
| 2008/0058525 | A1 | 3/2008 | Allen et al. |
| 2008/0187866 | A1 | 8/2008 | Cheon et al. |
| 2008/0238967 | A1 | 10/2008 | Busch et al. |
| 2009/0137389 | A1 | 5/2009 | Cheon et al. |
| 2010/0016154 | A1 | 1/2010 | Chu et al. |

FOREIGN PATENT DOCUMENTS

| | | |
|---|---|---|
| EP | 0107780 | 5/1984 |
| EP | A-0 568 344 | 11/1993 |
| EP | A 0576015 | 12/1993 |
| EP | A-0 591 106 | 4/1994 |
| EP | 0588344 B1 | 3/2000 |
| EP | A 1234681 | 8/2002 |
| EP | A-1 491 590 | 12/2004 |
| GB | 1298462 | 12/1972 |
| GB | A-2 031 600 | 4/1980 |
| GB | 2311 075 A | 9/1997 |
| JP | 49 023007 A | 3/1974 |
| JP | 56 027393 A | 3/1981 |
| JP | 58 038192 A | 3/1983 |
| JP | 59062666 | 4/1984 |
| JP | 62288828 | 12/1987 |
| JP | 04 016382 A | 1/1992 |
| JP | 04213368 | 8/1992 |
| JP | 05 255340 A | 10/1993 |
| JP | 06 103790 A | 4/1994 |
| JP | 07076587 | 3/1995 |
| JP | 07304972 | 11/1995 |
| WO | WO 02/096665 | 12/2002 |
| WO | WO 2004/078875 A | 9/2004 |

OTHER PUBLICATIONS

"Imaging Processes and Materials", Neblette's Eighth Edition, J. Sturge, V.Walworth, A. Shepp, Eds., Van Nostrand Reinhold, 1989, pp. 274-275.

Ian Fletcher and Rudolf Zink, "Synthesis and Properties of Phthalide-type Color Formers", in "Chemistry and Applications of Leuco Dyes", Ramaiah Muthyala, Ed., Plenum Press, New York, 1997, pp. 97-123.

PCT International Search Report (PCT/US06/18450) Date of Mailing Sep. 25, 2007.

PCT International Search Report (PCT/US06/18386) Date of Mailing Jun. 20, 2008.

EPO European Search Report—(06759686.6) Date of completion of search Feb. 6, 2009.

"Rhodamine dyes and related compounds", Zhurnal Organicheskoi Khimii, 1972, vol. 8, pp. 1725-1729, XP009111705.

"Bestimmung der Quantenausbeute der Rubinfluoreszenz bei Anregung durch Einstrahlung in eine blauen Absorptionslinien", Zeitschrift Fuer Physik, 1962, vol. 167, pp. 446-451, XP009111706.

U.S. Appl. No. 12/573,850, filed Oct. 5, 2009, Vetterling et al.

U.S. Appl. No. 12/750,539, filed Mar. 30, 2010, Cheon et al.

Compounds with RN 846606-85-1 and RN 879669-29-1 published in 1914.

Beilstein Institute for Organic Chemistry, Frankfurt-Main, Germany; (1988-2001); XP-002290704, pp. 1-4.

Beilstein Institute for Organic Chemistry, Frankfurt-Main, Germany; (1988-2001); XP-002290705, pp. 1-2.

Beilstein Institute for Organic Chemistry, Frankfurt-Main, Germany; (1988-2001); XP-002290706, pp. 1-2.

Beilstein Institute for Organic Chemistry, Frankfurt-Main, Germany; (1988-2001); XP-002290707, pp. 1-2.

Beilstein Institute for Organic Chemistry, Frankfurt-Main, Germany; (1988-2001); XP-002290708, pp. 1-2.

Mizutani et al., "Hydrogen-bonding-based thermochromic phenol-amine complexes", *Journal of Physical Organic Chemistry*, (1998), 11:737-742.

Non-final Office Action (U.S. Appl. No. 11/433,810) dated Jul. 9, 2008.

Orban et al., "Formation of Hydrogen-bonded Complexes between Phenol and Some Heterocyclic Bases in Carbon Tetrachloride", *J. Chem. Soc. Perkin Trans. II* (1987), pp. 1815-1817.

PCT International Search Report (PCT/US04/05986) Date of Mailing Sep. 15, 2004.

PCT International Search Report (PCT/US06/18386) Date of Mailing Jun. 20, 2008.

PCT International Search Report—(PCTUS09/32443) Date of Mailing Mar. 3, 2009.

Savvin et al, "Mechanism of action of cationic surfactants in Organic reagent-metal ion-surfactant systems", (1978), 33(8)pp. 1473-1480.

Siegel et al., "Infrared study of the interaction between proton donors and 1,10-phenanthroline derivatives", *Spectrochimica Acta*, (1989), 45A:1297-1304.

Spencer et al., "Hydrogen Bond Equilibria of Phenol-Pyridine in Cyclohexane CCl$_4$, and Benzene Solvents", *J. Phys. Chem.* (1987), pp. 1673-1674.

Titov et al., "Equilibria of bisphenol complexation with pyridine in acetonitrile solutions", *Zhurnal Obshchei Khimii* (1993), pp. 1869-1871. Journal written in Russian. English Abstract.

Yoshihiro Hatano, "The Chemistry of Fluoran Leuco Dyes", Ramaiah Muthyala, Ed., Plenum Press, New York, 1997, pp. 180-191.

Ioffe, et al., "Zhurnal Organicheskoi Khimii", 1972, 8(8), pp. 1726-1729 (in Russia).

STN Search report and Abstract of Ioffe, et al., "Zhurnal Organicheskoi Khimii", 1972, 8(8), pp. 1726-1729.

PCT International Search Report—(PCTUS09/69464) Date of Mailing Mar. 30, 2010.

Notice of Allowance, U.S. Appl. No. 11/433,808, Date of Mailing Jun. 25, 2010.

COLOR-FORMING COMPOUNDS AND USE THEREOF IN IMAGING MEMBERS AND METHODS

REFERENCE TO RELATED APPLICATIONS

This application is a continuation-in-part of copending U.S. patent application Ser. No. 11/433,810, filed on May 12, 2006, entitled "Novel Rhodamine Dyes" and of copending U.S. patent application Ser. No. 11/433,808, filed May 12, 2006, entitled "Thermal Imaging Members and Methods", the disclosures of which are hereby incorporated by reference herein in their entirety.

This application is related to the following commonly assigned United States patent applications and patents, the disclosures of all of which are hereby incorporated by reference herein in their entirety:

U.S. Pat. No. 6,801,233 B2 which describes and claims a thermal imaging system for use in the present invention;

U.S. Pat. No. 7,008,759 B2 which describes and claims color-forming compositions for use in the present invention;

U.S. Pat. No. 7,176,161 B2 which describes and claims color-forming compositions for use in the present invention;

U.S. Pat. No. 7,282,317 B2 which describes and claims color-forming compositions for use in the present invention;

U.S. patent application Ser. No. 11/400,734, filed Apr. 6, 2006, which describes and claims an imaging method for use in the present invention;

U.S. Pat. No. 7,408,563, which describes and claims an imaging method for use in the present invention;

U.S. patent application Ser. No. 12/022,955, filed Jan. 30, 2008, entitled "Printhead pulsing techniques for multicolor printers"; and U.S. patent application Ser. No. 12/022,969, filed Jan. 30, 2008, entitled "Thermal Imaging Members and Methods".

FIELD OF THE INVENTION

This invention relates to novel compounds and, more particularly, to compounds which exhibit one color in the crystalline form and a second, different color in the liquid, or amorphous, form. Also described are imaging members and methods, including thermal imaging members and methods, utilizing the compounds.

BACKGROUND OF THE INVENTION

The development of thermal printing heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal printing heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal printing head will normally be higher than the temperature needed to cause coloration during the long storage time. Actually reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be higher than the lamination temperature by as small a margin as possible, as would be the case for time-independent temperature of coloration.

Finally, the imaging system may comprise more than one color-forming layer and be designed to be printed with a single thermal printing head, as described in the above-mentioned patent application Ser. No. 10/151,432. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204-5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274-275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633. U.S. Pat. Nos. 4,390,616 and 4,436,920 describe image forming members comprising materials similar to those of the present invention. The materials described therein are fluoran dyes for use in conjunction with a developer, and there is not a report of image formation upon melting in the absence of a developer.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

As the state of the art in imaging systems advances and efforts are made to provide new imaging systems that can meet new performance requirements, and to reduce or eliminate some of the undesirable characteristics of the known systems, it would be advantageous to have new compounds which can be used as image-forming materials in imaging systems, including thermal imaging systems.

SUMMARY OF THE INVENTION

It is therefore an object of this invention to provide novel compounds.

Another object of the invention is to provide compounds which exhibit a different color when in the crystalline form than when in the amorphous form (which may be a liquid).

Yet another object of the invention is to provide imaging members and methods, including thermal imaging members and methods, which utilize the novel compounds.

The present invention provides novel rhodamine compounds that are useful as image dyes in imaging systems. According to one aspect of the invention there are provided novel color-forming compounds that are colorless when in the crystalline form and exhibit the conjugated rhodamine chromophore when in the amorphous form (which may be a liquid).

In one embodiment of the invention there are provided novel color-forming compounds that are represented by formula (I):

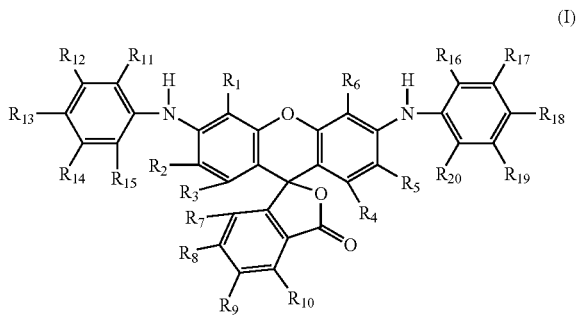

wherein:
$R_1$-$R_{10}$ are alkyl or hydrogen;
at least one of $R_{11}$, $R_{15}$, $R_{16}$ and $R_{20}$ is alkyl or halogen;
at least one of $R_{11}$, $R_{13}$, $R_{15}$, $R_{16}$, $R_{18}$ and $R_{20}$ is fluorine;

and $R_{11}$-$R_{20}$ are chosen from the group consisting of hydrogen, alkyl, substituted alkyl, halogen, alkoxy, and substituted carbonyl.

The conversion to the amorphous form can be carried out by applying heat to the compounds and therefore the compounds are useful in thermal imaging members used in thermal imaging methods. In such thermal imaging methods thermal energy may be applied to the thermal imaging members by any of the techniques known in thermal imaging such as from a thermal print head, a laser, a heated stylus, etc. In another embodiment, the conversion to the amorphous form may be effected by applying a solvent for the crystalline solid such as from an ink jet imaging apparatus to at least partially dissolve the crystalline material.

In yet another embodiment one or more thermal solvents, which are crystalline materials, can be incorporated into the thermal imaging member in close proximity to crystals of the compounds of the invention. The crystalline thermal solvent(s), upon being heated, melt and dissolve or liquefy, and thereby convert, at-least partially, the crystalline image-forming compound of the invention to the amorphous form, thereby forming an image.

The compounds of the invention may be incorporated in any suitable thermal imaging members. Typical suitable thermal imaging members generally comprise a substrate carrying at least one image-forming layer including a compound of the invention in the crystalline form, which can be converted, at least partially, to an amorphous form, the amorphous form having intrinsically a different color from the crystalline form. The thermal imaging member may be monochrome or multicolor. The temperature at which an image is formed in at least one of the image-forming layers is preferred to be substantially time-independent.

Preferred thermal imaging members include those having the structures described in above-mentioned U.S. Pat. Nos. 6,801,233 and 7,176,161.

DEFINITIONS

Figure 1:
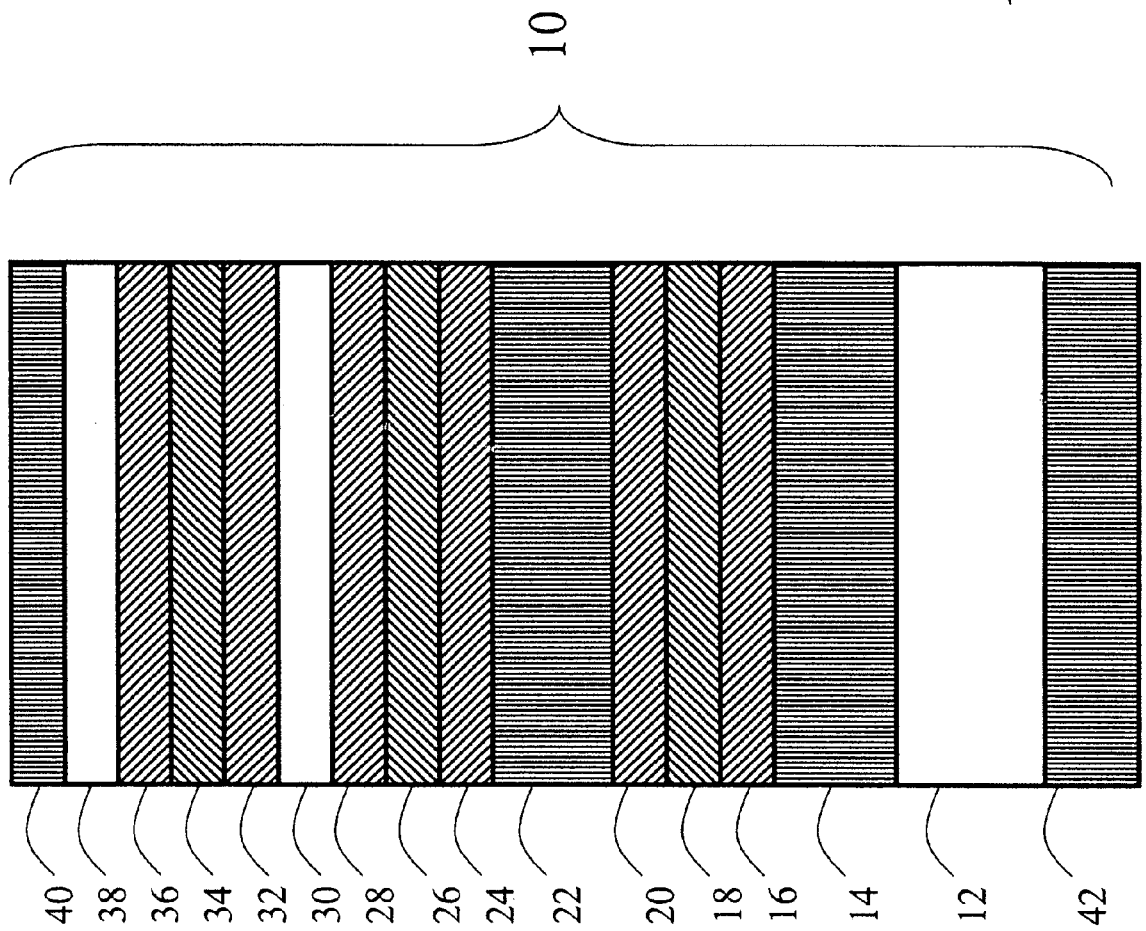
FIG. 1 is a schematic, side sectional view of a three-color thermal imaging member according to the invention.

The term "alkyl", as used herein refers to saturated straight-chain, branched-chain or cyclic hydrocarbon radicals. Examples of alkyl radicals include, but are not limited to, methyl, ethyl, propyl, isopropyl, n-butyl, tert-butyl, neopentyl, n-hexyl, cyclohexyl, n-octyl, n-decyl, n-dodecyl and n-hexadecyl radicals.

The term "alkenyl" as used herein refers to unsaturated straight-chain, branched-chain or cyclic hydrocarbon radicals. Examples of alkenyl radicals include, but are not limited to, allyl, butenyl, hexenyl and cyclohexenyl radicals.

The term "alkynyl" as used herein refers to unsaturated hydrocarbon radicals having at least one carbon-carbon triple bond. Representative alkynyl groups include, but are not limited to, ethynyl, 1-propynyl, 1-butynyl, isopentynyl, 1,3-hexadiynyl, n-hexynyl, 3-pentynyl, 1-hexen-3-ynyl and the like.

The terms "halo" and "halogen", as used herein, refer to an atom selected from fluorine, chlorine, bromine and iodine.

The term "aryl", as used herein, refers to a mono-, bicyclic or tricyclic carbocyclic ring system having one, two or three aromatic rings including, but not limited to, phenyl, naphthyl, anthryl, azulyl, tetrahydronaphthyl, indanyl, indenyl and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl", as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "carbonyl" as used herein refers to a carbonyl group, attached to the parent molecular moiety through the carbon atom, this carbon atom also bearing a hydrogen atom, or in the case of a "substituted carbonyl" a substituent as described in the definition of "substituted" below.

The term "acyl" as used herein refers to groups containing a carbonyl moiety. Examples of acyl radicals include, but are not limited to, formyl, acetyl, propionyl, benzoyl and naphthyl.

The term "alkoxy", as used herein, refers to a substituted or unsubstituted alkyl, alkenyl or heterocycloalkyl group, as previously defined, attached to the parent molecular moiety through an oxygen atom. Examples of alkoxy radicals include, but are not limited to, methoxy, ethoxy, propoxy, isopropoxy, n-butoxy, tert-butoxy, neopentoxy and n-hexoxy.

The term "aryloxy" as used herein refers to a substituted or unsubstituted aryl or heteroaryl group, as previously defined, attached to the parent molecular moiety through an oxygen atom. Examples of aryloxy include, but are not limited to, phenoxy, p-methylphenoxy, naphthoxy and the like.

The term "alkylamino", as used herein, refers to a substituted or unsubstituted alkyl, alkenyl or heterocycloalkyl group, as previously defined, attached to the parent molecular moiety through a nitrogen atom. Examples of alkylamino radicals include, but are not limited to, methylamino, ethylamino, hexylamino and dodecylamino.

The term "arylamino", as used herein, refers to a substituted or unsubstituted aryl or heteroaryl group, as previously defined, attached to the parent molecular moiety through a nitrogen atom.

The term "substituted" as used herein in phrases such as "substituted alkyl", "substituted alkenyl", "substituted aryl", "substituted heteroaryl", "substituted heterocycloalkyl", "substituted carbonyl", "substituted alkoxy", "substituted acyl", "substituted amino", "substituted aryloxy", and the like, refers to independent replacement of one or more of the hydrogen atoms on the substituted moiety with substituents independently selected from, but not limited to, alkyl, alkenyl, heterocycloalkyl, alkoxy, aryloxy, hydroxy, amino, alkylamino, arylamino, cyano, halo, mercapto, nitro, carbonyl, acyl, aryl and heteroaryl groups.

DETAILED DESCRIPTION OF THE INVENTION

Compounds in the crystalline state commonly have properties, including color, that are very different from those of the same compounds in an amorphous form. In a crystal, a molecule is typically held in a single conformation (or, more rarely, in a small number of conformations) by the packing forces of the lattice. Likewise, if a molecule can exist in more than one interconverting isomeric form (such forms being referred to in the art as "tautomers"), only one of such isomeric forms is commonly present in the crystalline state. In the amorphous state or in solution, on the other hand, the compound may explore its whole conformational and isomeric space, and only a small proportion of the population of individual molecules of the compound may at any one time exhibit the particular conformation or isomeric form adopted in the crystal. Compounds of the present invention exhibit tautomerism in which at least one tautomeric form is colorless, and at least another tautomeric form is colored. The crystalline form of compounds of the present invention comprises predominantly the colorless tautomer.

According to the invention, there have been provided molecules exhibiting tautomerism in which at least one tautomeric form is colorless, and at least another tautomeric form is colored. Crystallization of the equilibrating mixture of the two tautomeric forms in solution is carried out so as to produce colorless crystals. The solvent chosen to perform the crystallization will typically be one of such polarity (and other chemical properties, such as hydrogen-bonding ability) that the pure colorless crystal form is favored, either in the equilibrium between the colorless and colored forms in solution, or in having lower solubility in the solvent than the colored form. The choice of solvent is usually determined empirically for a particular mixture of tautomers.

As discussed in more detail below, the substituents of the preferred compounds of the present invention are chosen so as to enable the colorless tautomer to be prepared in a practical manner in the form of colorless crystals.

Upon conversion of the pure crystalline colorless form to the amorphous form, the equilibrium between the two tautomers is re-established. The proportion of the amorphous material that is colored (i.e., the proportion that is in the colored tautomeric form) may vary, but is preferably at least about 10%. The proportion (expressed as a percentage) of the total amorphous material that is colored (in the absence of any other materials) is hereinafter referred to as the "% coloration" of the color-forming compound. The substituents of the preferred compounds of the present invention are chosen so as to maximize the % coloration without sacrificing the ability to form colorless crystals in a practical manner.

The colored and colorless tautomeric forms of the molecules of the present invention must meet certain criteria for image quality and permanence. The colorless form, which is preferably the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored, amorphous form should be stable also to the above-mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For nonphotographic applications, however, it may be required that the colored form not be one of the subtractive primary colors, but rather a particular spot color (for example, orange, blue, etc.).

The novel compounds of the present invention are most useful as magenta color-formers, i.e., materials absorbing light in the green region of the electromagnetic spectrum. The wavelength of maximum absorption for such compounds is ideally between 540 and 550 nm, and the shape of the absorption curve is preferably such that minimal blue light (wavelengths below about 500 nm) and red light (wavelengths above about 600 nm) are absorbed.

The melting points of the compounds determine how the compounds may be used in thermal imaging members. For example, in a three-color thermal imaging member such as is disclosed in the above-mentioned U.S. Pat. No. 6,801,233 B2, the layer that is imaged in the shortest time, but with the highest temperature at the surface of the imaging member, typically has an activation temperature above 200° C. The layer that is imaged with an intermediate surface temperature, for an intermediate time, typically has an activation temperature of about 150-180° C. The layer that is imaged with the lowest surface temperature, for the longest time, typically has an activation temperature of about 90-130° C.

As discussed in more detail below, color-forming molecules of the present invention whose activation temperatures are not ideal, but which otherwise meet the requirements for incorporation into a thermal imaging member, may be used in conjunction with thermal solvents (crystalline compounds that, when melted, dissolve the color-forming molecule of the present invention). In such cases, the activation temperature may be determined by the melting point of the thermal solvent.

Another important property of the color-forming compounds of the present invention is the glass transition temperature, Tg. In order for the image formed by the amorphous color-former to be stable against recrystallization back to the crystalline form, preferably the glass transition temperature ($T_g$) of the amorphous mixture of the color-former (if used alone) should be higher than any temperature that the final image must survive. Typically, it is preferred that the $T_g$ of the amorphous, colored material be at least about 50° C., and ideally above about 60° C.

A first embodiment of the present invention is a compound whose colorless tautomer is represented by formula (I) as described above. Representative compounds according to the invention are those of formula (I) shown in Table I, below. The dyes are listed in the order of decreasing % coloration in the amorphous form.

TABLE I

| Dye # | R1-R10, R12, R15 | R11 | R13 | R14 | R16 | R17 | R18 | R19 | R20 |
|---|---|---|---|---|---|---|---|---|---|
| 1 | H | Me | F | H | Me | H | OMe | H | H |
| 2 | H | Me | F | H | Me | H | H | H | Me |
| 3 | H | Me | Me | H | Et | H | H | H | Me |

TABLE I-continued

| Dye # | R1-R10, R12, R15 | R11 | R13 | R14 | R16 | R17 | R18 | R19 | R20 |
|---|---|---|---|---|---|---|---|---|---|
| 4 | H | Me | F | H | Et | H | H | H | H |
| 5 | H | Me | F | H | Me | H | Me | H | H |
| 6 | H | F | Me | H | Me | H | F | H | H |
| 7 | H | Me | F | H | Me | H | H | Me | H |
| 8 | H | Me | F | H | Me | F | H | H | H |
| 9 | H | Me | F | H | Me | H | H | F | H |
| 10 | H | Me | F | H | Me | H | H | F | H |
| 11 | H | F | Me | H | H | H | F | H | H |
| 12 | H | Me | F | H | Me | H | F | H | H |
| 13 | H | F | F | H | Me | H | H | Me | H |
| 14 | H | Me | OMe | H | Et | H | H | H | Me |
| 15 | H | F | Me | H | Me | H | OMe | H | H |
| 16 | H | F | F | H | Me | H | H | H | Me |
| 17 | H | F | Me | H | Me | H | Me | H | H |
| 18 | H | Me | F | H | Me | H | CONPr2 | H | H |
| 19 | H | F | Me | H | F | H | Me | H | H |
| 20 | H | F | Me | H | i-Pr | H | H | H | H |
| 21 | H | F | F | H | i-Pr | H | H | H | H |
| 22 | H | F | F | H | Et | H | H | H | H |
| 23 | H | Me | F | H | F | H | H | H | H |
| 24 | H | F | Me | H | Me | H | H | Me | H |
| 25 | H | F | Me | H | Et | H | H | H | H |
| 26 | H | F | H | H | Me | H | H | Me | H |
| 27 | H | F | Me | H | Me | H | H | H | Me |
| 28 | H | F | H | H | Me | H | H | H | Me |
| 29 | H | F | Me | H | Me | H | H | H | H |
| 30 | H | F | H | H | i-Pr | H | H | H | H |
| 31 | H | F | H | H | Me | H | Cl | H | H |
| 32 | H | F | H | H | Me | H | H | H | H |
| 33 | H | Me | OMe | H | OMe | H | H | H | H |
| 34 | H | F | F | H | Me | H | H | F | H |
| 35 | H | F | Me | H | Me | F | H | H | H |
| 36 | H | Me | F | H | OMe | H | H | H | H |
| 37 | H | F | Me | H | Me | H | H | F | H |
| 38 | H | F | H | H | Me | H | H | F | H |
| 39 | H | F | H | H | F | Me | H | H | H |
| 40 | H | Me | Me | H | OMe | H | H | H | H |
| 41 | H | F | Me | H | F | H | H | H | H |
| 42 | H | F | H | H | F | H | H | H | H |
| 43 | H | F | Me | H | OMe | H | H | H | H |
| 44 | H | Me | F | H | OEt | H | H | H | H |
| 45 | H | F | Me | H | OEt | H | H | H | H |
| 46 | H | F | H | H | OEt | H | H | H | H |
| 47 | H | Cl | Me | H | Cl | H | Me | H | H |

Some relevant physical properties of Dyes 1-47 are shown below in Table II. In some instances a property was not measured, as indicated by N/A in the Table.

TABLE II

| Dye # | $\lambda_{max}$ (film) | Color | MP (° C.) | Tg (° C.) | Heat of Fusion (J/g) | Amorphous coloration (%) | Crystallinity |
|---|---|---|---|---|---|---|---|
| 1 | 548 | Purple | 218.38 | 115.74 | 74.09 | 80% | Amorphous |
| 2 | 544 | Magenta | N/A | N/A | N/A | 70% | Amorphous |
| 3 | 552 | N/A | N/A | N/A | N/A | 58% | Amorphous |
| 4 | 546 | Pink | 161.25 | 106.14 | 45.09 | 53% | Crystalline |
| 5 | 546 | Pink | 237.77 | 116.77 | 69.53 | 52% | Crystalline |
| 6 | 544 | Purple | 249.48 | 101.01 | 72.65 | 51% | Crystalline |
| 7 | 546 | Pink | 212.35 | 115.29 | 59.6 | 50% | Crystalline |
| 8 | 544 | Magenta | N/A | N/A | N/A | 47% | Amorphous |
| 9 | 552 | Pink | 235.27 | 113.72 | 64 | 47% | Crystalline |
| 10 | 544 | Magenta | N/A | N/A | N/A | 45% | Amorphous |
| 11 | 554 | Purple | >260 | N/A | N/A | 45% | Crystalline |
| 12 | 544 | Magenta | 221.5 | 115.85 | 62.53 | 43% | Crystalline |
| 13 | 546 | Pink | 225.17 | 107.5 | 74.12 | 42% | Crystalline |
| 14 | 548 | N/A | N/A | N/A | N/A | 41% | Crystalline |
| 15 | 550 | Red | 234.43 | 108.26 | 71.46 | 41% | Crystalline |
| 16 | 542 | Pink | 176.43 | 123.78 | 45.61 | 40% | Crystalline |
| 17 | 548 | Red | 247.16 | 109.33 | 86.99 | 39% | Crystalline |
| 18 | 544 | N/A | 230 | N/A | N/A | 36% | Crystalline |

TABLE II-continued

| Dye # | $\lambda_{max}$ (film) | Color | MP (° C.) | Tg (° C.) | Heat of Fusion (J/g) | Amorphous coloration (%) | Crystallinity |
|---|---|---|---|---|---|---|---|
| 19 | 546 | Pink | 261.88 | 104.27 | 88.1 | 36% | Crystalline |
| 20 | 548 | Pink | 203 | 101.41 | 65.04 | 36% | Crystalline |
| 21 | 544 | Pink | 213.8 | 91.02 | 66.18 | 35% | Crystalline |
| 22 | 544 | Pink | 172.60 | 98.84 | 52.81 | 35% | Crystalline |
| 23 | 546 | Pink | 218 | 106.31 | 68.23 | 33% | Crystalline |
| 24 | 550 | Pink | 199.11 | 108.73 | 62.13 | 33% | Crystalline |
| 25 | 550 | Red | 208.85 | 92.92 | 66.94 | 29% | Crystalline |
| 26 | 546 | White | 210.69 | 104.64 | 72.32 | 28% | Crystalline |
| 27 | 546 | Pink | 121.03, 173.32 | 124.39 | 14.36, 39.15 | 26% | Solvate |
| 28 | 542 | Pink | 133.47 | 124.83 | 67.43 | 24% | Crystalline |
| 29 | 546 | Pink | 222.41 | 107.68 | 78.5 | 23% | Crystalline |
| 30 | 548 | Pink | 102.44 | 88.28 | 101.5 | 23% | Solvate |
| 31 | 544 | Pink | 245.42 | 109.18 | 80.48 | 19% | Crystalline |
| 32 | 546 | White | 192.37 | 105.11 | 62.39 | 18% | Crystalline |
| 33 | 554 | Pink | 219.1 | 104.85 | 74.83 | 17% | Crystalline |
| 34 | 540 | White | 210.35 | 103.89 | 68.9 | 16% | Crystalline |
| 35 | 544 | Magenta | N/A | N/A | N/A | 16% | Amorphous |
| 36 | 550 | Pink | 151.55 | 108.22 | 35.85 | 16% | Crystalline |
| 37 | 546 | Pink | 209.38 | 103.69 | 64.65 | 15% | Crystalline |
| 38 | 544 | White | 239.48 | 104.02 | 85.25 | 14% | Crystalline |
| 39 | 544 | Magenta | N/A | N/A | N/A | 13% | Amorphous |
| 40 | 554 | Pink | 198.43 | 106.89 | 56.31 | 13% | Crystalline |
| 41 | 546 | Pink | 243.93 | 109.88 | 78.08 | 9% | Crystalline |
| 42 | 544 | Magenta | 235 | N/A | N/A | 7% | Crystalline |
| 43 | 556 | Pink | 98.56 | 99.56 | 63.75 | 7% | Solvate |
| 44 | 548 | Pink | 177.07 | 98.32 | 50.95 | 6% | Crystalline |
| 45 | 560 | White | 180.6 | 93.56 | 66.69 | 0% | Crystalline |
| 46 | N/A | White | 196.52 | 92.88 | 65.82 | 0% | Crystalline |
| 47 | N/A | Magenta | 177.47, 208.06 | 104 | 8.18, 31.89 | N/A | Solvate |

In Table II, the term "color" refers to the isolated crystals when it is indicated that the compound is crystalline. When such crystals are described as "pink", they may be appropriate for incorporation into a thermal imaging member, since the pink coloration may result from slight residual amorphous material that may become invisible when the crystals are incorporated into a thin film. Typically, a color-forming layer in a thermal imaging member of the present invention comprises about 0.1-1 g/m² of a color-forming compound of the present invention, in the form of crystals less than about 1 micrometer in diameter.

In some cases, the crystals that are formed from color-forming compounds are solvates, as indicated in Table II. Solvate crystals may exhibit inferior stability to crystals of the pure material, and may be difficult to obtain in a reproducible manner. It is preferred that the crystalline form of compounds of the present invention comprise crystals of the pure material, not including any of the solvent of crystallization, when these materials are intended for incorporation into a thermal imaging member.

The present inventors have found that it is generally impossible to obtain colorless, crystalline materials from compounds of formula (I) (i.e., compounds in which both nitrogen atoms bonded to the xanthene nucleus bear one hydrogen atom) unless at least one of $R_{11}$, $R_{15}$, $R_{16}$ and $R_{20}$ (the ortho substituents on the phenyl rings) is not hydrogen, and preferably alkyl or halogen (preferably fluorine). It is hypothesized that the presence of ortho substituents bulkier than hydrogen impedes hydrogen-bonding association between color-forming molecules that favors the colored tautomer and therefore makes the preparation of colorless crystals difficult (although this is a hypothesis only and not intended to limit the scope of the invention in any way).

Colorless compounds of formula (I) (a tautomeric form also referred to herein as the "closed form") may also exist as a colored tautomer illustrated by formula (II) (also referred to herein as the "open form"):

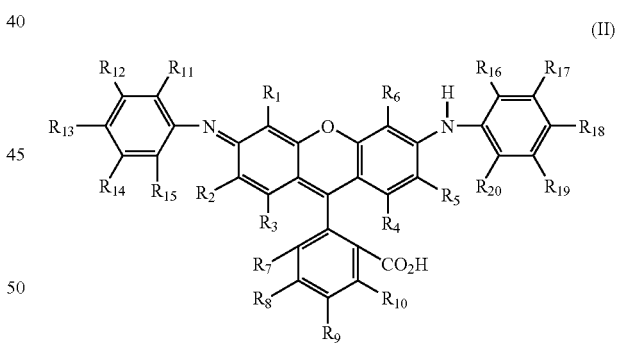

(II)

wherein $R_1$-$R_{20}$ are as defined above with respect to formula (I).

Compounds of formula (II) typically exhibit maximum absorption of light in the range of 500-600 nm. As such, these compounds are typically magenta dyes. The quality of the magenta chromophore is difficult to predict a priori in the current state of the imaging art, and moreover may be dependent upon the environment of the compound. Factors such as the dielectric constant and pH of the environment may profoundly affect the chromophore, both by direct perturbation and by facilitating aggregation of more than one dye molecule, as is well known in the art.

Nevertheless, it been found that, in the case where the compounds of the present invention are intended as magenta dyes in a photographic application, the presence of a single ortho substituent bulkier than hydrogen on at least one of the phenyl rings results in a sharper absorption peak and a superior magenta chromophore than would be the case where all four ortho substituents on the phenyl rings are hydrogen. It is not preferred that both ortho substituents on a particular phenyl ring be bulkier than hydrogen, however, since in this case it is thought that steric hindrance may cause twisting of the phenyl ring out of the plane of the xanthene chromophore, resulting in a perturbation to the chromophore.

The present inventors have also found that it is difficult to predict the degree of amorphous coloration from the structure of a compound of formula (I). Nevertheless, in general, when each phenyl ring bears an ortho substituent that is a hydrogen bond acceptor (such as fluorine or alkoxy) the degree of amorphous coloration has been found to be low (see, for example, dyes 39, 41, 42, 43, 45 and 46 in Tables I and II).

If neither of the phenyl rings bears an ortho substituent that is a hydrogen bond acceptor, conversely, the degree of amorphous coloration is typically high (see, for example, dyes 1-5). In such cases, however, it may be difficult to maintain the material in the colorless, crystalline form, if this can even be prepared at all.

It is therefore especially preferred for only one of the two phenyl rings to bear an ortho substituent that is a hydrogen bond acceptor, and preferably this substituent is fluorine. Stated otherwise, it is especially preferred that exactly one of substituents $R_{11}$, $R_{15}$, $R_{16}$ and $R_{20}$ be fluorine.

To form a direct thermal imaging system, the crystalline, colorless form of the compounds of the invention is made into a dispersion in a solvent in which the compound is insoluble or only sparingly soluble, by any of the methods known in the art for forming dispersions. Such methods include grinding, attriting, etc in order to reduce the particle size of the crystals. The particular solvent chosen will depend upon the particular crystalline material. Solvents that may be used include water, organic solvents such as hydrocarbons, esters, alcohols, ketones, nitrites, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrollidone) and cellulose derivatives, water-dispersed latices such as styrene/butadiene or poly(urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art. These include slot, gravure, Mayer rod, roll, cascade, spray, and curtain coating techniques. The image-forming layer so formed is optionally overcoated with a protective layer or layers.

According to the present invention, the compounds of formula (I) may be incorporated into any thermal imaging members and used in any thermal imaging methods, including direct thermal imaging members and thermal transfer imaging members and methods.

In one embodiment of the present invention, as discussed above, one or more thermal solvents, which are crystalline materials, can be incorporated in the thermal imaging member. The crystalline thermal solvent(s), upon being heated, melt and thereafter dissolve or liquefy the crystalline color-forming material of formula (I), thereby converting it to the amorphous form and providing a color change (i.e., an image). Thermal solvents may be advantageously used when it is required for a color-forming layer in a direct thermal imaging member to have an activation temperature (the temperature at which color is formed or at which color changes) that is lower than the melting point of the compound of formula (I). The melting point of the thermal solvent, rather than that of the compound of formula (I), may in such a case establish the activation temperature of a color-forming layer.

It will be clear to one of ordinary skill in the art that the activation temperature of a color-forming layer that comprises a mixture of crystalline materials may be different from the melting points of any of the individual components. A eutectic mixture of two crystalline components, for example, melts at a lower temperature than either of the components in isolation. Conversely, if the rate of solubilization of the compound of formula (I) in the molten thermal solvent is slow, the activation temperature of the mixture may be higher than the melting point of the thermal solvent. Recall that the activation temperature of a mixture of a compound of formula (I) and a thermal solvent is the temperature at which the color of the mixture changes, i.e., the temperature at which a sufficient amount of the compound of formula (I) dissolves in the molten thermal solvent to provide a visible color change. It will be clear from the above discussion that the activation temperatures of mixtures of compounds of formula (I) and thermal solvents may be dependent upon the rate of heating. For these reasons, in the design of thermal imaging members of the present invention determination of the actual activation temperature of a composition is preferred to be carried out experimentally.

Any suitable thermal solvents may be incorporated in the thermal imaging members of the invention. Suitable thermal solvents include, for example, aromatic and aliphatic ethers, diethers and polyethers, alkanols containing at least about 12 carbon atoms, alkanediols containing at least about 12 carbon atoms, monocarboxylic acids containing at least about 12 carbon atoms, esters and amides of such acids, aryl amides, especially benzanilides, aryl sulfonamides and hydroxyalkyl-substituted arenes.

Specific preferred thermal solvents include: 1,2-diphenoxyethane, 1,2-bis(4-methylphenoxy)ethane, tetradecan-1-ol, hexadecan-1-ol, octadecan-1-ol, dodecane-1,2-diol, hexadecane-1,16-diol, myristic acid, palmitic acid, stearic acid, methyl docosanoate, 1,4-bis(hydroxymethyl)benzene, diaryl sulfones such as diphenylsulfone, 4,4'-dimethyldiphenylsulfone, phenyl p-tolylsulfone and 4,4'-dichlorodiphenylsulfone, and p-toluenesulfonamide.

Particularly preferred thermal solvents are ethers such as 1,2-bis(2,4-dimethylphenoxy)ethane, 1,4-bis(4-methylphenoxymethyl)benzene, bis(4-phenoxyphenoxymethyl)benzene and 1,4-bis(benzyloxy)benzene.

It is possible that the dissolution of the compounds of formula (I) by a thermal solvent may lead to an amorphous form (in which the compound is dissolved in the amorphous thermal solvent) in which the proportion of the open, colored form is different from the proportion that would be present in the amorphous form resulting from melting the compound of formula (I) alone (i.e., without interaction with the thermal solvent). In particular, the proportion of the open, colored form of the compound in the amorphous material may be enhanced by use of hydrogen-bonding or acidic thermal solvents. Materials that increase the proportion of the color-forming material that is in the open, colored form are hereinafter referred to as "developers". It is possible that the same compound may serve the function of thermal solvent and developer.

Preferred developers include phenols such as 4,4'-butylidenebis[2-(1,1-dimethylethyl)-5-methyl-phenol], 2,2'-methylenebis(6-tert-butyl-4-methylphenol), 2,2'-methylenebis(6-tert-butyl-4-ethylphenol), 2,2'-ethylidenebis(4,6-di-tert-butylphenol), bis[2-hydroxy-5-methyl-3-(1-methylcyclohexyl)phenyl]methane, 1,3,5-tris(2,6-dimethyl-3-hydroxy-4-tert-butylbenzyl) isocyanurate, 2,6-bis[[3-(1,1-dimethylethyl)-2-hydroxy-5-methylphenyl]methyl]-4-methylphenol, 2,2'-butylidenebis[6-(1,1-dimethylethyl)-4-methylphenol, 2,2'-(3,5,5-trimethylhexylidene)bis(4,6-dimethyl-phenol], 2,2'-methylenebis[4,6-bis(1,1-dimethylethyl)-phenol, 2,2'-(2-methylpropylidene)bis[4,6-dimethyl-phenol], 1,1,3-tris(2-methyl-4-hydroxy-5-t-butylphenyl)butane, tris(3,5-di-t-butyl-4-hydroxybenzyl) isocyanurate, 2,2'-thiobis(4-tert-octylphenol), and 3-tert-butyl-4-hydroxy-5-methylphenyl sulfide.

In order for the image formed by the amorphous color-former to be stable against recrystallization back to the crystalline form, preferably the glass transition temperature (Tg) of the amorphous mixture of the color-former and any thermal solvent should be higher than any temperature that the final image must survive. Typically, it is preferred that the Tg of the amorphous, colored material be at least about 50° C., and ideally above about 60° C. In order to ensure that the Tg is sufficiently high for a stable image to be formed, materials having a high Tg may be added to the color-forming composition. Such materials, hereinafter referred to as "stabilizers", when dissolved in the amorphous mixture of color-former, optional thermal solvent, and optional developer, serve to increase the thermal stability of the image.

Preferred stabilizers have a Tg that is at least about 60° C., and preferably above about 80° C. Examples of such stabilizers are the aforementioned 1,3,5-tris(2,6-dimethyl-3-hydroxy-4-tert-butylbenzyl) isocyanurate (Tg 123° C.) and 1,1,3-tris(2-methyl-4-hydroxy-5-t-butylphenyl)butane (Tg 101° C.). The stabilizer molecule may also serve as a thermal solvent or as a developer.

For example, the color-forming material may itself have a melting temperature above the desired temperature for imaging, and a Tg (in the amorphous form) of about 60° C. In order to produce a color-forming composition melting at the desired temperature, it may be combined with a thermal solvent that melts at the desired temperature for imaging. The combination of thermal solvent and color-forming material may, however, have a Tg that is substantially lower than 60° C., rendering the (amorphous) image unstable. In this case, a stabilizer such as 1,3,5-tris(2,6-dimethyl-3-hydroxy-4-tert-butylbenzyl) isocyanurate may be added, to raise the Tg of the amorphous material. In addition, there may be provided a developer, for example, a phenolic compound such as 2,2'-ethylidenebis(4,6-di-tert-butylphenol), in order to increase the proportion of the color-forming material that is in the colored form in the amorphous phase.

Preferably the color-forming compound of the present invention, the (optional) thermal solvent, the (optional) developer and the (optional) stabilizer are each predominantly in their crystalline forms prior to imaging. By "predominantly" is meant at least about 50% and preferably more than that. During imaging, at least one of these materials melts and an amorphous mixture of the materials is formed. The amorphous mixture is colored, whereas the crystalline starting materials are not.

The temperature range over which melting (and therefore coloration) occurs should be as narrow as possible, especially in the case that the compounds of the present invention are incorporated into a thermal imaging member capable of forming full-color images. It is preferred that the temperature range of melting (as measured by differential scanning calorimetry) of a color-forming composition comprising a compound of the present invention be less than 15° C. as measured at the half height of the peak, and preferably less than 10° C. measured at half height.

As mentioned above, color-forming compounds of the present invention are most appropriate for affording magenta coloration. In one preferred thermal imaging member of the present invention the magenta color-forming layer is the middle of three color-forming layers, and has an ideal activation temperature onset of between 145° C. and 160° C.

Two preferred color-forming compositions of the present invention are:

a. a mixture of Dye 23 of the present invention (1 part by weight), 1,4-bis(4-methylphenoxymethyl)benzene (a thermal solvent, 5 parts by weight), 4,4'-butylidenebis[2-(1,1-dimethylethyl)-5-methyl-phenol] (a developer, 2 parts by weight), 1,3,5-tris(2,6-dimethyl-3-hydroxy-4-tert-butylbenzyl) isocyanurate (a stabilizer, 0.5 parts by weight), and a polymeric binder, for example, poly(vinyl alcohol) (2-5 parts by weight) (onset of melting 149° C., range of melting measured at half height 9° C.); and b. a mixture of Dye 23 of the present invention (1 part by weight), 1,4-bis(4-phenoxyphenoxymethyl)benzene (a thermal solvent, 5 parts by weight), 4,4'-butylidenebis[2-(1,1-dimethylethyl)-5-methyl-phenol] (a developer, 2 parts by weight), 1,3,5-tris(2,6-dimethyl-3-hydroxy-4-tert-butylbenzyl) isocyanurate (a stabilizer, 0.5 parts by weight), and a polymeric binder, for example, poly(vinyl alcohol) (2-5 parts by weight) (onset of melting 152.5° C., range of melting measured at half height 6.58° C.).

It is possible that one of the components in the amorphous, colored mixture may recrystallize after the image has been formed. It is desirable that such recrystallization not change the color of the image. In the case that a color-former, thermal solvent, developer and stabilizer are used, the thermal solvent may typically recrystallize without greatly affecting the color of the image.

The substituents on the compounds of formula (I) are preferably chosen to minimize the water solubility of the compounds and facilitate the formation of a colorless form in non-polar, non-protic solvents. This is because the manufacture of a thermal imaging member of the present invention typically involves an aqueous coating process. Were the compound of formula (I) to dissolve appreciably in water (the coating solvent), the coloration that is intended to occur when heating the thermal imaging member itself would occur prematurely during manufacture. On the other hand, the thermal solvents, when used, are typically non-polar, non-protic solvents, and are intended to dissolve the compounds of formula (I).

Yet another consideration is the stability of the image formed by the compound of formula (I). When used in a direct thermal imaging member, the colorless form of the compound (formula (I) itself) and the colored form of the compound (formula (II)) each must be stable, since in such imaging members the material is present both in colored and uncolored regions. In particular, the forms represented by formulas I and II must be stable to ultraviolet light and to oxidation in the presence or absence of light of any wavelength. The present inventors have found that the light stability of the colorless form of compounds of the present invention is maximized when each nitrogen atom attached to the xanthene nucleus bears an aryl group and a hydrogen atom, as shown in formula (I). Note that some compounds of the prior art bear alkyl substituents on at least one of these nitrogen atoms. Such alkyl groups may be prone to removal by photooxidation, leading to coloration of the colorless crystals in the presence of light and oxygen.

A particularly preferred compound of formula (I), meeting all the above-mentioned requirements, is Dye 23. As shown in Example IX, below, Dye 23 exhibits the best light stability in the colorless crystalline form of the compounds tested.

The compounds used according to the invention may be prepared by synthetic processes which are known to those skilled in the art, particularly in view of the state of the art in organic synthetic processes, and the present disclosure and specific preparatory examples provided below herein.

Generally, symmetrical rhodamine dyes can be prepared in one step from 3',6'-dichlorofluorans by reacting two equivalents of an aromatic or aliphatic amine as described in U.S. Pat. No. 4,602,263, GB2311075 and DE81056.

Alternatively, the unsymmetrical rhodamines can be prepared by use of an alternate synthetic pathway in which one equivalent of an aniline or other aromatic amine is reacted selectively with the 3',6'-dichlorofluoran using aluminum chloride as a catalyst to produce 3'-chloro-6'-N-arylfluorans. These products may be isolated and purified, or may be directly reacted with a second aromatic amine. Zinc chloride or another Lewis acid may be used as the catalyst for the second addition. DE139727 describes the selective addition of anilines to 3',6'-dichlorofluorans to produce 3'-chloro-6'-arylaminofluorans using a mixture of zinc chloride and zinc oxide at 160° C.

Unsymmetrical rhodamines can also be made from 2-benzoyl benzoic acid derivatives by condensation with 3-arylamino phenols as described in Chemistry and Applications of Leuco Dyes, pp. 180-191 R. Muthyala, Ed., Plenum Press, New York and London, 1997 and also U.S. Pat. Nos. 4,390,616 and 4,436,920.

To optimize the chromophore, melting point, degree of coloration, light stability and solubility of the dyes in this application a variety of aromatic amines are utilized.

The aromatic amines used in this application are typically commercially available, or may be synthesized by reduction of the corresponding nitro compounds.

3',6'-dichlorofluoran is synthesized from fluorescein using thionyl chloride and dimethylformamide in a variation of the method of Hurd described in the Journal of the Amer. Chemical Soc. 59, 112 (1937).

Careful recrystallization of the color-forming materials of formula (I) from solvent mixtures such as heptanes/acetone, water/acetone, heptanes/ethyl acetate, heptanes/toluene, or single solvents such as toluene produces colorless crystalline material which is preferred for use in thermal imaging members.

Examples of the preparation of preferred compounds of the present invention are given below.

Referring now to FIG. 1, a preferred thermal imaging member 10 according to the invention is shown in schematic form. All layers were coated from aqueous fluids which contained small amounts of a coating aid, Zonyl FSN, available from Dupont Co., Wilmington, Del.

The substrate 12 is a filled, white, oriented polypropylene base of thickness about 200 microns, FPG200, available from Yupo Corporation America, Chesapeake, Va. 23320.

An adhesion-promoting layer 14 overlies the substrate 12, composed of the CP655 (a latex available from Dow Chemical Co., Midland, Mich., 48% by weight), CP692 (a latex available from Dow Chemical Co., Midland, Mich., 31% by weight) and POVAL MP103 (a fully hydrolyzed poly vinyl alcohol) available from Kuraray America, Inc., New York, N.Y., 21% by weight). This layer has a coverage of 7.5 g/m2.

Overlying the adhesion-promoting layer 14 is an oxygen barrier layer 16 composed of the above-mentioned POVAL MP103 (89.3% by weight) and glyoxal (a crosslinker, 10.7% by weight). This layer has a coverage of 1.2 g/m2.

Overlying the oxygen barrier layer 16 is a cyan color-forming layer 18 composed of a cyan color-former having melting point 210° C., Dye X of copending U.S. patent application Ser. No. 12/022,969 (1 part by weight), 1,2-bis(2,4-dimethylphenoxy)ethane (a thermal solvent having melting point 112° C., coated as an aqueous dispersion of crystals having average particle size under 1 micron, 6 parts by weight), a phenolic antioxidant/developer (Anox 29, having melting point 161-164° C., available from Chemtura, Middlebury, Conn., coated as an aqueous dispersion of crystals having average particle size under 1 micron, 1 part by weight), Lowinox 1790 (a second phenolic antioxidant/stabilizer, available from Chemtura, Middlebury, Conn. coated as an aqueous dispersion of crystals having average particle size under 1 micron, 1.5 parts by weight), a binder (poly(vinyl alcohol), Celvol 205, available from Celanese, Dallas, Tex., 7 parts by weight) and glyoxal (0.42 parts by weight). This layer has a coverage of 3.35 g/m2.

Overlying the cyan color-forming layer 18 is a barrier layer 20 that contains a fluorescent brightener. This layer is composed of the above-mentioned POVAL MP103 (82% by weight), glyoxal (8% by weight) and Leucophor BCF P115 (a fluorescent brightener, available from Clariant Corp., Charlotte, N.C., 10% by weight). This layer has a coverage of 2 g/m2.

Overlying the barrier layer 20 is a thermally-insulating interlayer 22 composed of the above-mentioned CP692(93% by weight) and the above-mentioned POVAL MP103 (7% by weight). This layer has a coverage of 27.5 g/m2.

Overlying the thermally-insulating interlayer 22 is a barrier layer 24 composed the above-mentioned POVAL MP103 (94% by weight) and glyoxal (a crosslinker, 6% by weight). This layer has a coverage of 1.5 g/m2.

Overlying the barrier layer 24 is a magenta color-forming layer 26, composed of a magenta color-former, Dye 23 of the present invention (1 part by weight); an a phenolic ether, 1,4-bis[(4-methylphenoxy)methyl]-benzene, (melting point 172° C.; coated as an aqueous dispersion of crystals having average particle size under 1 micron, 5 parts by weight, a phenolic antioxidant/developer (Lowinox 44B25, having melting point 210-211° C., available from Chemtura, Middlebury, Conn., coated as an aqueous dispersion of crystals having average particle size under 1 micron, 2 parts by weight), Lowinox 1790 (a second phenolic antioxidant/stabilizer, available from Chemtura, Middlebury, Conn., coated as an aqueous dispersion of crystals having average particle size under 1 micron, 0.5 part by weight), a binder (poly(vinyl alcohol, Celvol 540, available from Celanese, Dallas, Tex., 3.2 parts by weight) and glyoxal (0.19 parts by weight). This layer has a coverage of 2.56 g/m2.

Overlying the magenta color-forming layer 26 is a barrier layer 28 that contains a fluorescent brightener. This layer is composed of the above-mentioned POVAL MP103 (82% by weight), glyoxal (8% by weight) and the above-mentioned Leucophor BCF P115. This layer has a coverage of 1 g/m2.

Overlying the barrier layer 28 is a second thermally-insulating interlayer 30 composed of the above-mentioned CP655 (48% by weight), the above-mentioned CP692 (31% by weight) and the above-mentioned POVAL MP103 (21% by weight). This layer has a coverage of 3 g/m2.

Overlying the second thermally-insulating interlayer 30 is a barrier layer 32 composed the above-mentioned POVAL MP103 (94% by weight) and glyoxal (a crosslinker, 6% by weight). This layer has a coverage of 1 g/m2.

Overlying the barrier layer 32 is a yellow color-forming layer 34 composed of Dye XI described in U.S. Pat. No. 7,279,264, (59.6% by weight, having melting point 202-203° C.), Lowinox 1790 (a phenolic antioxidant/stabilizer, available from Chemtura, Middlebury, Conn., coated as an aqueous dispersion of crystals having average particle size under 1 micron, 7.6% by weight), a binder (poly(vinyl alcohol), Celvol 540, available from Celanese, Dallas, Tex., 32.8% by weight). This layer has a coverage of 1.99 g/m2.

Overlying the yellow color-forming layer 34 is a barrier layer 36 composed of a fully hydrolyzed poly(vinyl alcohol), Celvol 325, available from Celanese, Dallas, Tex. (94% weight) and glyoxal (6% by weight). This layer has a coverage of 0.5 g/m2.

Deposited on the barrier layer 36 is an ultra-violet blocking layer 38 composed of a nanoparticulate grade of titanium dioxide (MS-7, available from Kobo Products Inc., South Plainfield, N.J., 62% by weight), the above-mentioned POVAL MP103 (35% by weight) and glyoxal (3% by weight). This layer has a coverage of 2 g/m2.

Deposited on the ultra-violet blocking layer 38 is an overcoat 40 composed of Carboset 526 (a polymeric binder available from Lubrizol Advanced Materials, Inc., Cleveland, Ohio, 5 parts by weight), the above-mentioned POVAL MP103 (2.12 parts by weight), NeoRez R-989 (a polyurethane latex, available from DSM NeoResins, Wilmington, Mass., 4.34 parts by weight), Hidorin F-115P (a meltable lubricant, available from Nagase America Corp., New York, N.Y., 5 parts by weight), Pinnacle 2530, a grade of erucamide, available from Lubrizol Advanced Materials, Inc., Cleveland, Ohio, (1 part by weight), and Ultraflon AD-10 (a poly(tetrafluoroethylene) lubricant available from Laurel Products LLC, Elverson, Pa., 1.72 parts by weight). This layer has a coverage of 1 g/m2.

On the reverse side of substrate 12 is an anticurl layer 42 comprising above-mentioned POVAL MP103 (94% by weight) and glyoxal (a crosslinker, 6% by weight). This layer has a coverage of 12-15 g/m2 and may contain a matting agent as is well known in the art.

The imaging members described above can be printed using techniques such as those described in U.S. Pat. No. 6,801,233, U.S. patent application Ser. No. 11/400,734, filed Apr. 6, 2006, U.S. Pat. No. 7,408,563, and U.S. patent application Ser. No. 12/022,955, entitled "Print Head Pulsing Techniques for Multicolor Printers" of even date herewith.

The invention will now be described further in detail with respect to specific embodiments by way of Examples, it being understood that these are intended to be illustrative only and the invention is not limited to the materials, amounts, procedures and process parameters, etc. recited herein. All parts and percentages recited are by weight unless otherwise specified.

EXAMPLE I

Dye 6 a. Preparation of 3'-chloro-6'-(4-fluoro-2-methylanilino)fluoran

To a solution of 3',6'-dichlorofluoran (1107 g, 3.00 mol) in sulfolane (6 L) was added with stirring anhydrous aluminum chloride (1600 g, 12.00 mol) at such a rate that the temperature of the batch did not exceed 100° C. Upon completion of the addition the reaction mixture was agitated with passive cooling until the temperature reached 85° C., at which point 4-fluoro-2-methylaniline (412.96 g, 3.3 mol) was added dropwise over 15 minutes, with the reaction being maintained at 85° C. by gentle heating. When this addition was complete, 2,6-lutidine (706.2 g, 6.60 mol) was added dropwise over the course of one hour, again maintaining the temperature at 85° C. At this point HPLC indicated that the starting dichlorofluoran had been consumed, so the reaction mixture was quenched into ice-water (40 liters) with vigorous stirring that was maintained for 16 hours. The resulting slurry was filtered and the cake washed with water (16 L), then sucked dry with a rubber dam. The still-damp cake was suspended in acetonitrile (8 L) and heated to reflux, being maintained at this temperature for an additional 15 minutes. The suspension, which became quite thick, was allowed to cool to 20° C. and the solid collected by vacuum filtration using a rubber dam. The compacted cake was washed with 2×4 liters of 30% (v/v) acetonitrile/water, dried under a dam, and finally dried in a vacuum oven overnight at 100° C. to provide a pale gray solid weighing 1348 g (98.1% crude yield) suitable for conversion to final dyes.

b. Preparation of 3'-(2,4-dimethylanilino)-6'-(4-fluoro-2-methylanilino)fluoran (Dye 6)

A mixture of 3'-chloro-6'-(4-fluoro-2-methylanilino)fluoran (2.0 g; 4.37 mmol), 2,4-dimethylaniline (1.10 g; 8.74 mmol), zinc chloride (2.4 g; 17.5 mmol), zinc oxide (0.71 g; 8.74 mmol), and sulfolane (10 g) was stirred with heating at 150° C. overnight. After cooling, the mixture was quenched into 2N hydrochloric acid (50 mL) to give a precipitate that was collected by filtration, washed with water, and dissolved into N,N-dimethylformamide (30 mL). This solution was then neutralized with aqueous ammonium hydroxide (15 mL NH$_4$OH and 15 mL H$_2$O) to give a precipitate that was collected by filtration. This crude product was purified by column chromatography (eluent: 5% methanol in CH$_2$Cl$_2$), followed by recrystallization with a mixture of acetone and hexanes to give 1.66 g white solid (70% yield).

EXAMPLE II

Dye 12

Preparation of 3',6'-bis(4-fluoro-2-methylanilino) fluoran (Dye 12)

A mixture of 3',6'-dichlorofluoran (19.45 g, 50 mmol), 4-fluoro-2-methylaniline (25.0 g, 200 mmol), zinc chloride (22 g, 161 mmol), and zinc oxide (6.60 g, 81 mmol) in sulfolane (100 mL) was stirred at 200° C. for three hours, then cooled to 110° C. over 30 min. The reaction mixture was quenched into a mixture of conc. hydrochloric acid (100 mL) and water (300 mL) to give a red precipitate that was collected by filtration, washed with water (150 mL), and suspended in methanol (200 mL). The suspension was heated to 60° C. and to it was added a solution of conc ammonium hydroxide (15 mL) in methanol (20 mL). The solids went completely into solution for a brief time, after which precipitation of the presumed free base form of the dye began. The slurry was stirred with cooling to 20° C. and maintained at that temperature for 12 hours, then filtered. The cake was washed with cold methanol (70 mL) and dried in vacuo overnight to give 25.48 g burgandy solid (93% crude yield). Half (12.74 g) of this material was taken up in acetone (40 mL) and diluted with hexanes (90 mL), scratched, and left at 5° C. for two days to deposit solid that was collected by filtration and washed with 25 mL portions of 20%, 10%, 5%, and 0% acetone in hexanes, then dried in vacuo overnight to provide 10.10 g pale purple prisms (79° recovery).

EXAMPLE III

Dye 18 a. Preparation of N,N-dipropyl-4-methyl-2-nitrobenzamide

To a mixture of 4-methyl-3-nitrobenzoic acid (36.23 g, 0.2 mmol), N,N-dimethylformamide (5 mL), and toluene (85 mL) was added with stirring thionyl chloride (30 mL, 48.8 g, 0.41 mole). The mixture was stirred at gentle reflux for four hours, then distilled to approximately half the volume (67.77 g residual net weight) to remove excess thionyl chloride. This solution was cooled to 20° C., and 22.6 grams of it (nominally 6.67 mmol) was added to a solution of N,N-di-n-propylamine (22.0 g, 0.22 mole) in ethyl acetate (100 mL) resulting in immediate formation of a slurry that was stirred at ambient temperature overnight. This was then quenched into water (150 mL). The organic layer was washed with cold 0.5 N hydrochloric acid (100 mL), then with 5% aqueous sodium bicarbonate, dried (MgSO4) and evaporated to give a colorless oil weighing 16.55 g (94.0%). This was characterized by proton and carbon nmr, as well as electrospray mass spectrum (M+1 at m/e 265.1).

b. Preparation of N,N-dipropyl-3-amino-4-methylbenzamide

Crude N,N-dipropyl-4-methyl-3-nitrobenzamide (16.35 g, nominally 61.9 mmol) was dissolved in ethanol (125 mL). To this solution was added iron powder (11.34 g, 200 mmol), then, with rapid stirring, was added 12N hydrochloric acid (42 mL) at such a rate as to maintain a temperature of 75° C. (required 10 minutes). The solution was stirred at 75° C. for an additional 10 minutes, then quenched into water (500 mL). This slurry was made basic (pH 14) by addition of aqueous potassium hydroxide. The resulting pudding-like slurry was stirred with ethyl acetate (300 mL) and filtered (slow). The organic layer of the filtrate was dried (K2CO3) and evaporated to a thick oil that solidified overnight to provide 14.27 g (98.5%) of a wa xy solid that was characterized by proton nmr.

c. Preparation of 3'-chloro-6'-(3-N,N-di-n-propylbenzamido-6-methylanilino)fluoran To a mixture of 3',6'-dichlorofluoran (3.69 g; 10.0 mmol) in sulfolane (25 g) was added at 100° C. anh. aluminum chloride (4.0 g, 30 mmol), then, portionwise over 5 min, was added N,N-dipropyl-3-amino-4-methylbenzamide (2.34 g, 10 mmol). To this mixture, still with stirring at 100° C., was added 2,6-lutidine (2.0 g, 18.7 mmol). The mixture was stirred at 110° C. for an additional hour, cooled to 45° C., and quenched into a mixture of ice (100 g) and 6N hydrochloric acid (120 mL) to give a purple-gray precipitate that was collected by filtration, washed with cold water (200 mL), and suspended in dichloromethane (200 mL). This mixture was washed with 5% aqueous sodium bicarbonate (70 mL), then with water (70 mL), and finally evaporated to a bluish-gray glass, weighing 4.92 g (86.8%), which was characterized by proton and carbon nmr.

d. Preparation of 3'-(3-N,N-di-n-propylbenzamido-6-methylanilino)-6'-(4-fluoro-2-methylanilino)-fluoran (Dye 18)

To a suspension of 3'-chloro-6'-(3-N,N-di-n-propylbenzamido-6-methylanilino)-fluoran (4.40 g, 7.7 mmol) and 4-fluoro-2-methylaniline (2.94 g, 23.5 mmol) in sulfolane at 90° C. was added anhydrous zinc chloride (5.33 g, 39.1 mmol), producing a dark red solution. The temperature was raised to 170° C. and the solution maintained at this temperature for four hours. The mixture was then heated at 185° C. for an additional 1.5 hours, cooled to 120° C., and quenched into cold 1N hydrochloric acid (150 mL) to give a dark red precipitate which was collected by filtration, washed with water (150 mL), and dried overnight in vacuo at 60° C. to give a dark red solid. This was taken up in dichloromethane (80 mL); to this mixture was added a solution of 14N ammonium hydroxide (5 mL) in acetone (25 mL). The resulting solution was filtered to remove particulates and then chromatographed (silica gel eluted with dichloromethane, then with 33%; 50%, and 75% ethyl acetate). The purest fractions were evaporated to give a pink foam which was crystallized from acetone/hexanes, affording 3.67 g (72.7%) of pale pink prisms, mp 228-230.5° C., which were characterized by proton and carbon nmr, as well as electrospray mass spectrometry (M+1 at m/e 656.3).

EXAMPLE IV

Dye 23

Preparation of 3'-(2-fluoroanilino)-6'-(4-fluoro-2-methylanilino)fluoran (dye 23)

Purified 3'-chloro-6'-(4-fluoro-2-methylanilino)fluoran (1.34 kg, 96 weight %, 2.82 mol), prepared as described in Example I above) was dissolved in sulfolane (5 L) at 90-110° C. Zinc chloride (2.0 kg, 14.7 mol, 5.2 eq.) was added at 110-130° C., followed by freshly distilled 2-fluoroaniline (900 g, 7.08 mol, 2.88 eq.) added at 130-150° C. The internal temperature was raised to 190° C. and the reaction stirred at this temperature for 18 hours. The reaction was cooled to about 100° C. and quenched into a mixture of ice (20 kg), water (10 L) and conc. hydrochloric acid (1000 mL) with vigorous stirring. Agitation was continued 18 hours as the mixture attained ambient temperature. The solids were filtered and washed with water (2×5 L). The resultant purple solid was added to ethyl acetate (3 L) and triethylamine (500 mL) under vigorous stirring, which was maintained for an additional 30 min. Heptanes (6 L) was added slowly and the mixture stirred an additional 2 hours. The solid was filtered and washed with heptanes/ethyl acetate 80/20 (3 L), then with heptanes (3 L). The crude solid was dried at 80° C. for 16 hours to provide ~1.4 kg of a dark pink solid. The crude dye was dissolved in THF (3 L) and diluted with toluene (12 L). Silica gel (1 kg) was added and the mixture stirred for 30 minutes, filtered, and washed with toluene/THF 80/20 (6 L). The volume of the solution was reduced to 8 L then heptanes (8 L) was added. The slurry was stirred for 18 hours, then filtered. The solid was washed with toluene/heptanes 1/1 (3 L), then with heptanes (3 L), and finally dried at 80° C. to provide the color-former as a pink solid (1.29 kg, 93%).

EXAMPLE V

Dye 31 a. Preparation of 3'-(2-fluoroanilino)-6'-chlorofluoran

A 500 mL liter flask was charged with sulfolane (150 mL) followed by 3',6'-dichlorofluoran (20 g, 54.17 mmol. 1.0 eq.) and stirred vigorously. Aluminum chloride (22 g, 165 mmole, 3.05 eq.) was added next in portions to keep the temperature between 85-90° C. 2-Fluoroaniline (15 g, 135 mmole, 2.46 eq.) was added dropwise and the temperature of the reaction was kept between 85-90° C. The reaction was allowed to stir for 30 minutes at temperature (85-90° C.) then poured into ice water (1.5 L) with rapid stirring. The precipitate was collected by vacuum filtration, and then washed with additional water (1.5 L) until the eluent became colorless. The red solid was dried under vacuum at room temperature overnight. The dry solid was dissolved in dichloromethane and chromatographed on silica gel using heptanes/ethyl acetate from 100/0 to 70/30 as an eluent to afford 3'-(2-fluoroanilino)-6'-chlorofluoran (20.4 g, 85%) as a white solid. The purity by HPLC was 98.5% by area. The dye was characterized by mass spectrometry, DSC-TGA and NMR spectroscopy.

b. Preparation of 3'-(4-chloro-2-methylanilino)-6'-(2-fluoroanilino)fluoran (dye 31)

A 250 mL liter flask was charged With sulfolane (75 mL) followed by 3'-(2-fluoroanilino)-6'-chlorofluoran (8.0 g, 18.02 mmol. 1.0 eq.) and stirred vigorously. The reaction was heated and zinc chloride (12 g, 90.2 mmole, 5.0 eq.) was added in portions when the temperature reached 80° C. 4-Chloro-2-methylaniline (8.4 g, 59.3 mmole, 3.3 eq.) was added in small portions when the temperature reached 120° C. The temperature of the reaction was increased to 160° C. and the reaction was allowed to stir 18 hours at this temperature. The reaction mixture was then cooled to 100-120° C., then poured into ice water (0.75 L) containing acetic acid (25 mL) with rapid stirring. The precipitate was collected by vacuum filtration, then washed with additional water (1 L) until the eluent became colorless. The red solid was dried under vacuum at room temperature overnight. The dry solid was partially dissolved in dichloromethane with added triethylamine (most of the product turned into a green insoluble form) and chromatographed on silica gel using heptanes/ethyl acetate from 100/0 to 70/30 as an eluent to afford the product (2.58 g, 26%). The solid was slurried in heptanes/acetone 50/50 (75 mL) for three hours, filtered, washed with heptanes/acetone 50/50 (10 mL) and dried under vacuum at 50° C. to afford 3'-(4-chloro-2-methylanilino)-6'-(2-fluoroanilino)fluoran, (1.55 g, 16%) as a pink solid. The purity by HPLC was >99% by area. The dye was characterized by mass spectrometry, DSC-TGA and NMR spectroscopy.

EXAMPLE VI

Dye 42

Preparation of 3',6'-bis(2-fluoroanilino) fluoran (dye 42)

To a solution of 3',6'-dichlorofluoran (37.0 g, 0.10 mole) in sulfolane (200 mL) was added with stirring anhydrous aluminum chloride (40.0 g, 0.30 mol). The mixture was heated to 90° C. and 2-fluoroaniline (66.0 g, 0.59 mol) was added dropwise with stirring over 5 min. The batch was held at 170° C. for 5 hours, then cooled to 100 C and quenched into 1000 mL 1N hydrochloric acid to give a red precipitate that was collected by filtration and washed with water (500 mL). The wet cake was suspended in ethyl acetate (200 mL) and stirred overnight with triethylamine (20 mL, 143 mmol) and water (100 mL). The resulting slurry was filtered and the cake washed with water (150 mL), with ethyl acetate (100 mL), and finally with 50% ethyl acetate/heptane (100 mL), then dried in vacuo overnight to provide 45.0 g (77%) of pale pink prisms.

EXAMPLE VII

Dye 43 a. Synthesis of 3'-(2-Methoxyanilino)-6'-chlorofluoran

A 250 mL liter flask was charged with sulfolane (50 mL) followed by 3',6'-dichlorofluoran (10 g, 27.8 mmol. 1.0 eq.) and the contents stirred vigorously. Aluminum chloride (9.0 g, 67.5 mmole, 3.0 eq.) was added next in portions to keep the temperature between 80-85° C. o-Anisidine (2-methoxyaniline) (5.6 g, 45.5 mmole, 1.63 eq.) was added dropwise and the temperature of the reaction was kept between 80-85° C. The reaction was allowed to stir for 30 minutes at temperature (80-85° C.) then poured into ice water (1 L) with rapid stirring. The precipitate was collected by vacuum filtration, and then washed with additional water (1 L) until the eluent became colorless. The purple solid was dried under vacuum at room temperature overnight. The dry solid was dissolved in dichloromethane with added triethylamine and chromatographed on silica gel using heptanes/ethyl acetate from 100/0 to 70/30 as an eluent to afford 3'-(2-methoxyanilino)-6'-chlorofluoran (15.7 g, 64%) as a white solid. The purity by HPLC was >99% by area. The dye was characterized by mass spectrometry, DSC-TGA, and NMR spectroscopy.

b. Synthesis of [3'-(2-methoxyanilino)-6'-(2-fluoro-4-methylanilino)fluoran] (dye 43)

To a 250 mL liter flask was added sulfolane (50 mL) followed by 3'-(2-methoxyanilino)-6'-chlorofluoran (6.0 g, 13.16 mmol. 1.0 eq.), and N,N',N',N'',N'''-pentamethyldiethylenetriamine (1.75 g, 10.1 mmol, 0.77 eq.). The mixture was stirred vigorously. The reaction was heated and zinc chloride (8.0 g, 58.8 mmole, 4.46 eq.) was added in portions when the temperature reached 80° C. 2-Fluoro-4-methylaniline (2.5 g, 19.98 mmole, 1.52 eq.) was added in small portions when the temperature reached 120° C. The temperature of the reaction was increased to 170° C. and the reaction was allowed to stir 18 hours at this temperature. The reaction mixture was then cooled to 100-120° C. then poured into a mixture of ice water (0.75 L) and acetic acid (25 mL) with rapid stirring. The precipitate was collected by vacuum filtration, and then washed with additional water (1 L) until the eluent became colorless. The red solid was dried under vacuum at room temperature overnight. The dry solid was partially dissolved in dichloromethane with added triethylamine (some of the product turns into a green form) and chromatographed on silica gel using heptanes/ethyl acetate from 100/0 to 60/40 as an eluent to afford the product (4.3 g, 60%). The solid was crystallized from heptanes/acetone 90/10 (75 mL) overnight, filtered, washed with heptanes/acetone 90/10 (20 mL), then heptanes (20 mL), and dried under vacuum at 50° C. to afford 3'-(2-methoxyanilino)-6'-(2-fluoro-4-methylanilino)fluoran (2.2 g, 31%) as a pink solid. The purity by HPLC was >99% by area. The dye was characterized by mass spectrometry, DSC-TGA and NMR spectroscopy.

EXAMPLE VIII

Dye 45 a. Synthesis of 3'-(2-ethoxyanilino)-6'-chlorofluoran

To a 500 mL liter flask was added sulfolane (150 mL) followed by 3',6'-dichlorofluoran (20 g, 54.17 mmol. 1.0 eq.) with vigorous stirring. Aluminum chloride (22 g, 165 mmole, 3.05 eq.) was added next in portions to keep the temperature between 80-85° C. o-Phenetidine (2-ethoxyaniline) (16 g, 116.6 mmole, 2.15 eq.) was added dropwise and the temperature of the reaction was kept between 80-85° C. The reaction was allowed to stir for 30 minutes at temperature (80-85° C.), then poured into ice water (1.5 L) with rapid stirring. The precipitate was collected by vacuum filtration, and washed with additional water (1.5 L) until the eluent became colorless. The red solid was dried under vacuum at room temperature overnight. The dry solid was dissolved dichloromethane with added triethylamine and chromatographed on silica gel using heptanes/ethyl acetate from 100/0 to 70/30 as an eluent to afford 3'-(2-ethoxyanilino)-6'-chlorofluoran (20.6 g, 81%) as a white solid. The purity by HPLC was >99% by area. The dye was characterized by mass spectrometry, DSC-TGA and NMR spectroscopy.

b. Preparation of 3'-(2-ethoxyanilino)-6'-(2-fluoro-4-methylanilino)fluoran (dye 45)

To a 250 mL liter flask was added sulfolane (60 mL) followed by 3'-(2-ethoxyanilino)-6'-chlorofluoran (7.0 g, 14.9 mmol. 1.0 eq.) with vigorous stirring. The reaction was heated and zinc chloride (10.5 g, 77.0 mmole, 5.17 eq.) was added in portions when the temperature reached 80° C. 2-Fluoro-4-methylaniline (6.25 g, 49.9 mmole, 3.35 eq.) was added in small portions when the temperature reached 120° C. The temperature of the reaction was increased to 170° C. and the reaction was allowed to stir 18 hours at this temperature. The reaction mixture was then cooled to 100-120° C. then poured into ice water (0.75 L) and acetic acid (25 mL) with rapid stirring. The precipitate was collected by vacuum filtration, then washed with additional water (1 L) until the eluent became colorless. The red solid was dried under vacuum at room temperature overnight. The dry solid was dissolved in dichloromethane with added triethylamine and chromatographed on silica gel using heptanes/ethyl acetate from 100/0 to 40/60 as an eluent to afford the product (3.4 g, 41%). The solid was crystallized from heptanes/acetone 90/10 (75 mL) overnight, filtered, washed with heptanes/acetone 90/10 (20 mL) then heptanes (20 ml) and dried under vacuum at 50° C. to afford 3'-(2-ethoxyanilino)-6'-(2-fluoro-4-methylanilino)fluoran (2.47 g, 30%) as a pink solid. The purity by HPLC was >99% by area. The dye was characterized by mass spectrometry, DSC-TGA and NMR spectroscopy.

EXAMPLE IX

Light Stability of Crystals

This example illustrates the improved photostability of coatings of colorless crystals of compounds of the present invention as compared to a representative compound of the prior art. Coatings were prepared as follows:

a. Preparation of a Dispersion of Crystals of the Color-Former.

A glass jar (1 oz size) containing zirconium oxide grinding beads (10 g) was charged with crystals of the color-former under test (2.0 g), a solution of poly(vinyl alcohol) (Elvanol 4016, available from DuPont Corporation, Wilmington, Del., 3.0 g of a 6.7% aqueous solution), deionized water (4.5 g), and methyl acetate (1.0 g), and the mixture was stirred magnetically for 18-24 hours to produce a fine dispersion.

b. Preparation of Coating Fluid.

The dispersion prepared as described in a. above (3.5 g) was combined with poly(vinyl alcohol) (Celvol 205, available from Celvol 205, available from Celanese, Dallas, Tex., 0.98 g of a 12.3% aqueous solution), Zonyl FSN (a coating aid, available from Dupont, Wilmington, Del., 0.045 g), Zonyl FSA (a coating aid, available from Dupont, Wilmington, Del., 0.045 g), glyoxal (a crosslinker, 0.15 g of a 5% aqueous solution) and deionized water (3.43 g).

c. Preparation of Coating.

The fluid prepared as described in b. above was coated onto a white, filled poly(ethyleneterephthalate) (PET) film base of 3 mil thickness (Melinex 339, available form Dupont Teijin films, Hopewell, Va.) that had been subcoated with poly(vinyl alcohol) (Celvol 325, available from Celanese, Dallas, Tex., 1 g/m$^2$) using a #10 Mayer rod to give a dried coating thickness of approximately 0.3 g/m$^2$ of the color-former.

This procedure was followed using four color-forming materials of the present invention as well as a control color-forming material (Dye IV of copending U.S. patent application Ser. No. 11/433,808, comprising an octyl grouping on one of the nitrogen atoms bonded to the xanthene nucleus).

The coatings so formed were exposed to fluorescent lighting (2500 ft. candles) in an oxygen atmosphere, and the time taken for the reflection optical density to rise 0.05 above its initial value (measured in days) was recorded. The results of this test are reproduced in Table III, below.

TABLE III

|  | Time (days) |
| --- | --- |
| Control | 0.51 |
| Dye 23 | 3.58 |
| Dye 31 | 1.08 |
| Dye 36 | 1.24 |
| Dye 42 | 1.55 |
| Dye 44 | 1.73 |

It can be seen that the photostability of the colorless crystalline form of the materials of the present invention is substantially superior to that of the control material. The best performance as measured in this test was that of Dye 23 of the present invention.

Although the invention has been described in detail with respect to various preferred embodiments, the present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All publications, patent applications, issued patents and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

We claim:

1. A compound represented by the formula (I):

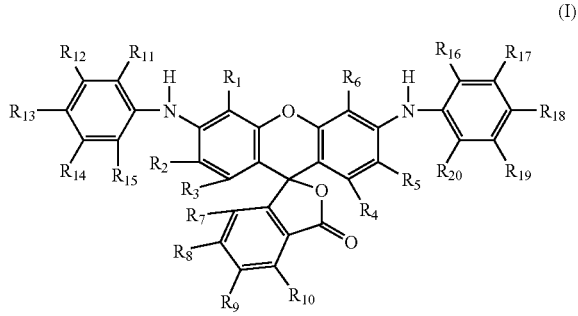

(I)

wherein:
$R_1$-$R_{10}$ are alkyl or hydrogen;
at least one of $R_{11}$, $R_{15}$, $R_{16}$ and $R_{20}$ is alkyl or halogen;
at least one of $R_{11}$, $R_{13}$, $R_{15}$, $R_{16}$, $R_{18}$ and $R_{20}$ is fluorine;
and $R_{11}$-$R_{20}$ are chosen from the group consisting of hydrogen, alkyl, substituted alkyl, halogen, alkoxy, and substituted carbonyl.

2. The compound of claim 1 in which:
$R_1$-$R_{10}$ are hydrogen;
at least one of $R_{11}$, $R_{15}$, $R_{16}$ and $R_{20}$ is alkyl or halogen;
at least one of $R_{11}$, $R_{13}$, $R_{15}$, $R_{16}$, $R_{18}$ and $R_{20}$ is fluorine;
and $R_{11}$-$R_{20}$ are chosen from the group consisting of hydrogen, alkyl, substituted alkyl, halogen, alkoxy, and substituted carbonyl.

3. The compound of claim 1 in which:
$R_1$-$R_{10}$ are hydrogen;
at least one of $R_{11}$, $R_{15}$, $R_{16}$ and $R_{20}$ is alkyl or fluorine;
at least one of $R_{11}$, $R_{12}$, $R_{13}$, $R_{14}$, and $R_{15}$ is fluorine;
at least one of $R_{16}$, $R_{17}$, $R_{18}$, $R_{19}$, and $R_{20}$ is fluorine;
and $R_{11}$-$R_{20}$ are chosen from the group consisting of hydrogen, alkyl, substituted alkyl, halogen, alkoxy, and substituted carbonyl.

4. The compound of claim 1 in which:
$R_1$-$R_{10}$, $R_{12}$, $R_{14}$, $R_{15}$ and $R_{17}$-$R_{20}$ are hydrogen;
$R_{11}$ is methyl; and
$R_{13}$ and $R_{16}$ are fluorine.

5. A thermal imaging composition comprising a compound represented by the formula (I):

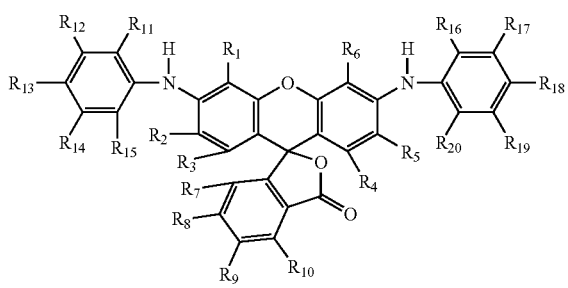

(I)

wherein:
$R_1$-$R_{10}$ are alkyl or hydrogen;
at least one of $R_{11}$, $R_{15}$, $R_{16}$ and $R_{20}$ is alkyl or halogen;
at least one of $R_{11}$, $R_{13}$, $R_{15}$, $R_{16}$, $R_{18}$ and $R_{20}$ is fluorine;
and $R_{11}$-$R_{20}$ are chosen from the group consisting of hydrogen, alkyl, substituted alkyl, halogen, alkoxy, and substituted carbonyl;
wherein said compound is in the crystalline form.

6. The thermal imaging composition as defined in claim 5 wherein said compound represented by formula (I) has a glass transition temperature of at least 50° C.

7. The thermal imaging composition as defined in claim 5 wherein said image-forming layer further comprises at least one thermal solvent.

8. The thermal imaging composition as defined in claim 7 wherein said thermal solvent is selected from the group consisting of 1,2-bis(2,4-dimethylphenoxy)ethane, 1,4-bis(4-methylphenoxymethyl)benzene, bis(4-phenoxyphenoxymethyl)benzene and 1,4-bis(benzyloxy)benzene, and mixtures thereof.

9. The thermal imaging composition as defined in claim 5 further comprising at least one compound comprising a phenolic grouping.

10. The thermal imaging composition as defined in claim 9 wherein said compound comprising a phenolic grouping is selected from the group consisting of 4,4'-butylidenebis[2-(1,1-dimethylethyl)-5-methyl-phenol], 2,2'-methylenebis(6-tert-butyl-4-methylphenol), 2,2'-methylenebis(6-tert-Butyl-4-Ethyl-Phenol), 2,2'-ethylidenebis(4,6-di-tert-butylphenol), bis[2-hydroxy-5-methyl-3-(1-methylcyclohexyl)phenyl]- methane, 1,3,5-tris(2,6-dimethyl-3-hydroxy-4-tert-butylbenzyl) isocyanurate, 2,6-bis[[3-(1,1-dimethylethyl)-2-hydroxy-5-methylphenyl]methyl]-4-methyl-phenol, 2,2'-butylidenebis[6-(1,1-dimethylethyl)-4-methyl-phenol, 2,2'-(3,5,5-trimethylhexylidene)bis[4,6-dimethyl-phenol], 2,2'-methylenebis[4,6-bis(1,1-dimethylethyl)-phenol, 2,2'-(2-methylpropylidene)bis[4,6-dimethyl-phenol], 1,1,3-tris(2-methyl-4-hydroxy-5-t-butylphenyl)butane, tris(3,5-di-t-butyl-4-hydroxybenzyl)isocyanurate, 2,2'-thiobis(4-tert-octylphenol), and 3-tert-butyl-4-hydroxy-5-methylphenyl sulfide.

11. A thermal imaging member comprising a substrate having first and second opposed surfaces, said first surface bearing a color-forming layer comprising a thermal imaging composition as defined in claim 5.

12. A thermal imaging method comprising (a) providing an imaging member as defined in claim 11; and (b) converting at least a portion of said compound to an amorphous form in an image-wise pattern whereby an image is formed.

13. The thermal imaging method as defined in claim 12 wherein step (b) comprises applying an image-wise pattern of thermal energy to said imaging member, said thermal energy being sufficient to convert at least some of said compound of formula (I) to an amorphous form.

\* \* \* \* \*